United States Patent
Oh et al.

(10) Patent No.: US 8,168,797 B2
(45) Date of Patent: May 1, 2012

(54) OXAZOLIDINONE DERIVATIVE WITH DIFLUOROPHENYL MOIETY, PHARMACEUTICALLY ACCEPTABLE SALT THEREOF, PREPARATION METHOD THEREOF AND ANTIBIOTIC COMPOSITION CONTAINING THE SAME AS AN ACTIVE INGREDIENT

(75) Inventors: Chang Hyun Oh, Seoul (KR); Jung Hyuck Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 693 days.

(21) Appl. No.: 12/277,364

(22) Filed: Nov. 25, 2008

(65) Prior Publication Data
US 2010/0069449 A1    Mar. 18, 2010

Related U.S. Application Data

(63) Continuation of application No. 12/313,625, filed on Nov. 20, 2008.

(30) Foreign Application Priority Data

Sep. 16, 2008    (KR) .................. 10-2008-0090659

(51) Int. Cl.
C07D 413/00 (2006.01)
C07D 263/00 (2006.01)
A61K 31/42 (2006.01)
A61K 31/421 (2006.01)

(52) U.S. Cl. .................. 548/216; 548/230; 514/376
(58) Field of Classification Search .................. None
See application file for complete search history.

(56) References Cited

FOREIGN PATENT DOCUMENTS
| | | |
|---|---|---|
| KR | 10-2006-0033300 A | 4/2006 |
| WO | WO 2007/093904 A1 | 8/2007 |
| WO | WO 2008/038092 A2 | 4/2008 |

OTHER PUBLICATIONS

Aliyenne et al., "Efficient synthesis of new chiral 1,2-benzothiazin-3-one 1,1-dioxide derivatives via lateral lithiation of 3-N-mesitylenesulfonyl-1,3-oxazolidin-2-ones." *Tetrahedron Letters* 49 (2008). 1473-1475.

Selvakumar et al., "Synthesis, SAR, and antibacterial activity of novel oxazolidinone analogues possessing urea functionality." *Bioorganic & Medicinal Chemistry Letters* 18 (2008). 856-860.

*Primary Examiner* — Yong Chong
*Assistant Examiner* — Jody Karol
(74) *Attorney, Agent, or Firm* — Ladas & Parry LLP

(57) ABSTRACT

Novel oxazolidinone derivatives with a difluorophenyl moiety, represented by Chemical Formula 1, pharmaceutically acceptable salts thereof, a preparation method thereof, and a pharmaceutical composition containing the same as an active ingredient are provided. Exhibiting potent inhibitory activity against Gram-positive bacteria including *Haemophilus influenza* and Coagulase negative staphylococci and resistant bacteria including vancomycin-resistant enterococci (VRE), the pharmaceutical composition is useful as an antibiotic

[Chemical Formula 1]

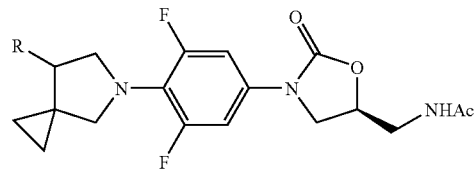

(wherein, R is as defined in the specification).

20 Claims, No Drawings

OXAZOLIDINONE DERIVATIVE WITH DIFLUOROPHENYL MOIETY, PHARMACEUTICALLY ACCEPTABLE SALT THEREOF, PREPARATION METHOD THEREOF AND ANTIBIOTIC COMPOSITION CONTAINING THE SAME AS AN ACTIVE INGREDIENT

CROSS-REFERENCE TO RELATED APPLICATION

This patent application is a continuation of U.S. application Ser. No. 12/313,625, filed on Nov. 20, 2008, which claims the benefit of priority from Korean Patent Application No. 10-2008-0090659 filed Sep. 16, 2008, the contents of which are incorporated herein by reference. To the extent appropriate, a claim of priority is made to each of the above disclosed applications.

BACKGROUND OF THE INVENTION

1. Field of the Invention

The present invention relates to novel oxazolidinone derivatives with a difluorophenyl moiety, pharmaceutically acceptable salts thereof, a method for preparing the same, and an antibiotic composition containing the same as an active ingredient.

2. Description of the Related Art

According to statistics in 1992, as many as 68% of methicillin-resistant *Staphylococcus aureus* (hereinafter referred to as "MRSA") strains show multidrug-resistance. Vancomycin, the most potent among currently available antibiotics, is the only antibiotic that is inhibitory of multidrug-resistant MRSA. However, a *Staphylococcus aureus* strain resistant to vancomycin was found in Japan in May, 1997. In fact, much earlier, in the 1980s, the emergence of vancomycin-resistant enterococci (hereinafter referred to as "VRE") had been reported from hospitals of the U.S.A. and Britain. In the U.S.A., VRE has increased to 13.6% in 1993 from 0.4% in 1989, and emerged as a hot topic in the medical world. Thus, the effectiveness of the glycopeptide type antibiotic vancomycin, which had been regarded as the last fortress against gram-positive bacteria, was called into doubt.

This great anxiety has disappeared with the emergence of linezolid. Food and Drug Administration (FDA) approval was granted for the antibiotic linezolid (U-100766) in April 2000. It is sold in the U.S. under the trade name Zyvox. Since the quinolone class, 35 years have passed before the development of this novel class antibiotic.

To date, a wide spectrum of various classes of antibiotics is available and various strains are also observed to have resistance thereto. With the expansion of the use of antibiotics, bacteria themselves undergo extensive mutations resulting in an explosive increase in resistance thereto. Furthermore, more frequent use of various antibiotics leads to a higher complexity of antibiotic resistance than in the past.

The antibiotic activity of the oxazolidinone class compounds was first discovered by researchers at E.I. DuPont. This company synthesized the oxazolidinonone compounds in 1987 and reported that Dup-721 showed inhibitory activity against Gram-negative anaerobes and *Mycobacterium tuberculosis* as well as gram-positive strains including MRSA and MRSE.

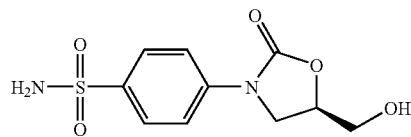

S-6123

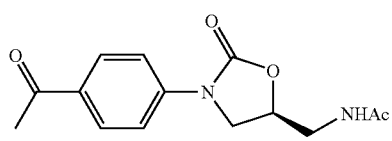

DuP-721

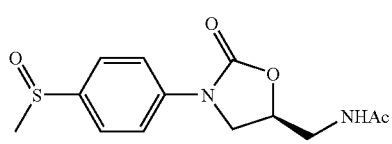

DuP-105

However, studies on Dup-105 and Dup-721 were not further undertaken because fatal toxicity was observed in conjunction therewith in Stage 1 of clinical testing conducted by Upjohn. Based on the finding that oxazolidinone compounds have antibacterial activity, Upjohn succeeded in developing antibiotic compounds U-100766 (Linezolid) and U-100562 (Eperezolid) in 1996. These compounds are similar to vancomycin in antibacterial activity against Gram-positive strains, but show very poor inhibitory activity against Gram-negative strains.

At this time, it is necessary to develop novel antibiotics as various bacterial strains are resistant to most antibiotics currently being used clinically. Particularly, novel oxazolidinone antibiotics are imperatively needed to circumvent the problem of resistant strains.

Culminating in the present invention, with the goal of overcoming the problems encountered in the prior art, intensive and thorough research was conducted by the present inventors into novel oxazolidinone class antibiotics with more potent anti-bacterial activity, which resulted in the finding that oxazolidinone derivatives with difluorophenyl moieties are highly inhibitory of resistant strains including Gram-positive bacteria and VRE.

SUMMARY OF THE INVENTION

It is therefore an object of the present invention to provide a novel oxazolidinone derivative and a pharmaceutically acceptable salt thereof.

It is another object of the present invention to provide a method for preparing the novel oxazolidinone derivative.

It is a further object of the present invention to provide an antibiotic composition containing the oxazolidinone derivative or the pharmaceutically acceptable salt thereof as an active ingredient.

In order to achieve the above object, the present invention provides a novel oxazolidinone derivative with a difluorophenyl moiety, represented by the following Chemical Formula 1, and a pharmaceutically acceptable salt thereof:

[Chemical Formula 1]

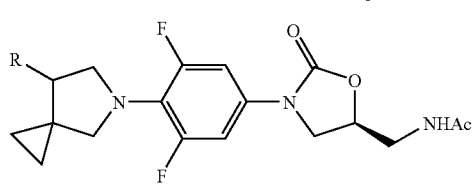

(wherein, R is hydroxy, amino, halogen, hydrazine, hydroxylamine, an alkyloxyimine of $C_1$~$C_4$ or allyloxyimine)

Also, the present invention provides a method for preparing the oxazolidinone derivative.

Further, the present invention provides an antibiotic composition containing the oxazolidinone derivative or a pharmaceutically acceptable salt thereof as an active ingredient.

DESCRIPTION OF THE PREFERRED EMBODIMENTS

A detailed description will be given of the present invention, below.

In accordance with an aspect thereof, the present invention provides a novel oxazolidinone derivative having a difluorophenyl moiety, represented by the following Chemical Formula 1.

[Chemical Formula 1]

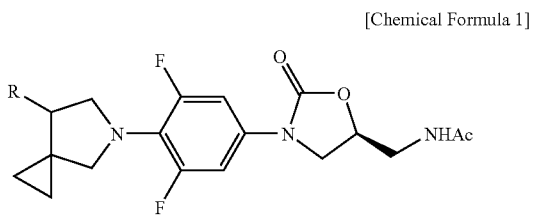

wherein, R is hydroxy, amino, halogen, hydrazine, hydroxyimine, an alkyloxyimine of $C_1$~$C_4$, or allyloxyimine.

Preferably, R is hydroxy, amino, fluoro, chloro, bromo, hydrazine, hydroxyimine, methoxyimine, ethoxyimine, propoxyimine, isopropoxyimine, butoxyimine, isobutoxyimine or allyloxyimine.

Concrete examples of the novel oxazolidinone derivatives with difluorophenyl moieties in accordance with the present invention include:

(1) (S)—N-{{3-[3,5-difluoro-4-(7-hydroxy-5-azaspiro[2,4]heptan-5-yl)phenyl]-2-oxo-5-oxazolidinyl}methyl}acetamide;

(2) (S)—N-{{3-[3,5-difluoro-4-(7-fluoro-5-azaspiro[2,4]heptan-5-yl)phenyl]-2-oxo-5-oxazolidinyl}methyl}acetamide;

(3) (S)—N-{{3-[3,5-difluoro-4-(7-hydroxyimino-5-azaspiro[2,4]heptan-5-yl)phenyl]-2-oxo-5-oxazolidinyl}methyl}acetamide;

(4) (S)—N-{{3-[3,5-difluoro-4-(7-methoxyimino-5-azaspiro[2,4]heptan-5-yl)phenyl]-2-oxo-5-oxazolidinyl}methyl}acetamide;

(5) (S)—N-{{3-[3,5-difluoro-4-(7-hydrazino-5-azaspiro[2,4]heptan-5-yl)phenyl]-2-oxo-5-oxazolidinyl}methyl}acetamide;

(6) (S)—N-{{3-[3,5-difluoro-4-(7-ethoxyimino-5-azaspiro[2,4]heptan-5-yl)phenyl]-2-oxo-5-oxazolidinyl}methyl}acetamide;

(7) (S)—N-{{3-[3,5-difluoro-4-(7-allyoxyimino-5-azaspiro[2,4]heptan-5-yl)phenyl]-2-oxo-5-oxazolidinyl}methyl}acetamide; and (8) (S)—N-{{3-[3,5-difluoro-4-(7-amino-5-azaspiro[2,4]heptan-5-yl)phenyl]-2-oxo-5-oxazolidinyl}methyl}acetamide.

Structures of the oxazolidinone derivatives of Chemical Formula 1 in accordance with the present invention are summarized in Table 1, below.

TABLE 1

| Cpd. | Structures |
| --- | --- |
| 1 | (structure with HC- spiro group, difluorophenyl, oxazolidinone-NHAc) |
| 2 | (structure with F on spiro group, difluorophenyl, oxazolidinone-NHAc) |
| 3 | (structure with =N-OH on spiro group, difluorophenyl, oxazolidinone-NHAc) |
| 4 | (structure with =N-OCH$_3$ on spiro group, difluorophenyl, oxazolidinone-NHAc) |
| 5 | (structure with =N-NH$_2$ on spiro group, difluorophenyl, oxazolidinone-NHAc) |
| 6 | (structure with =N-OC$_2$H$_5$ on spiro group, difluorophenyl, oxazolidinone-NHAc) |

TABLE 1-continued

| Cpd. | Structures |
|------|------------|
| 7 | (structure with allyloxyimino spiro pyrrolidine, difluorophenyl, oxazolidinone-NHAc) |
| 8 | (structure with H₂N-spiro pyrrolidine, difluorophenyl, oxazolidinone-NHAc) |

The oxazolidinone derivatives according to the present invention, represented by Chemical Formula 1, may be used in the form of pharmaceutically acceptable salts. Within the range of these salts are included, for example, acid addition salts formed with pharmaceutically acceptable free acids. As the free acids, non-toxic inorganic acids such as hydrochloric acid, bromic acid, sulfonic acid, phosphoric acid, etc., and non-toxic organic acids such as citric acid, acetic acid, lactic acid, maleic acid, fumaric acid, gluconic acid, methanesulfonic acid, glycolic acid, succinic acid, tartaric acid, 4-toluenesulfonic acid, galucturonic acid, embonic acid, glutamic acid, aspartic acid, etc. are useful, with preference for hydrochloric acid or methanesulfonic acid.

It should be understood that in addition to the oxazolidinone derivatives of Chemical Formula 1 and pharmaceutically acceptable salts thereof, solvates, hydrates and racemates that can be prepared therefrom are included within the scope of the present invention.

The acid addition salts of the compounds according to the present invention may be prepared using a typical method, for example, by dissolving the compound of Chemical Formula 1 in a water-miscible organic solvent, e.g., acetone, methanol, ethanol, or acetonitrile, adding excess organic acid or excess inorganic acid in water thereto to form precipitates or crystals. Subsequently, the solvent or excess acid is evaporated, followed by drying or suction filtering the precipitates to prepare acid addition salts thereof.

In accordance with another aspect thereof, the present invention provides a method for preparing the novel oxazolidinone derivative.

The method for preparing the novel oxazolidinone derivative of the present invention, as illustrated in Reaction Scheme 1, comprises:

Reacting a compound of Chemical Formula 2 with trifluoronitrobenzene of Chemical Formula 3 to give a compound of Chemical Formula 4 (Step 1);

Reducing the compound of Chemical Formula 4 through hydrogenation to a compound of Chemical Formula 5 (Step 2);

Introducing a carbobenzyloxy (CBZ) group into the amine group of the compound of Chemical Formula 5 to give a compound of Chemical Formula 6 (Step 3);

Adding n-butyl lithium and (R)-glycidyl butyrate to the compound of Chemical Formula 6 to give a compound of Chemical Formula 7 (Step 4);

Mesylating the hydroxy group of the compound of Chemical Formula 7 to give a compound of Chemical Formula 8 (Step 5);

Azidating the compound of Chemical Formula 8 with sodium azide to a compound of Chemical Formula 9 (Step 6);

Reducing and acetylating the compound of Chemical Formula 9 to a compound of Chemical Formula 10 (Step 7);

Deprotecting the compound of Chemical Formula 10 to give a compound of Chemical Formula 11 (Step 8); and Reducing the compound of Chemical Formula 11 to a compound of Chemical Formula 1a (Step 9).

[Reaction Scheme 1]

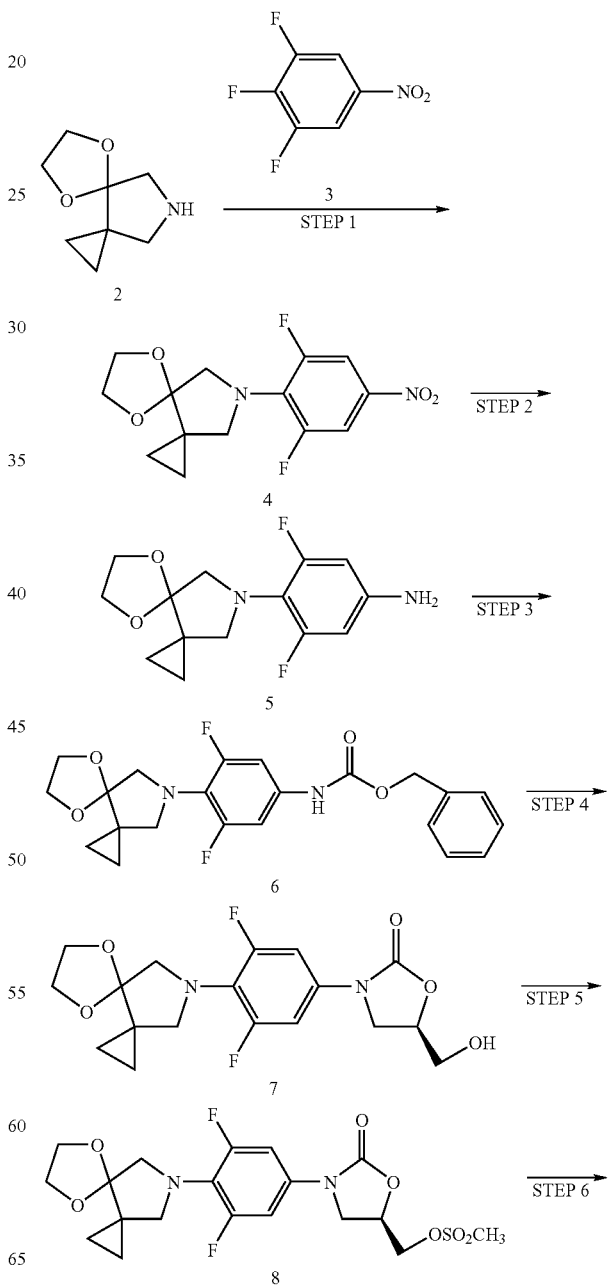

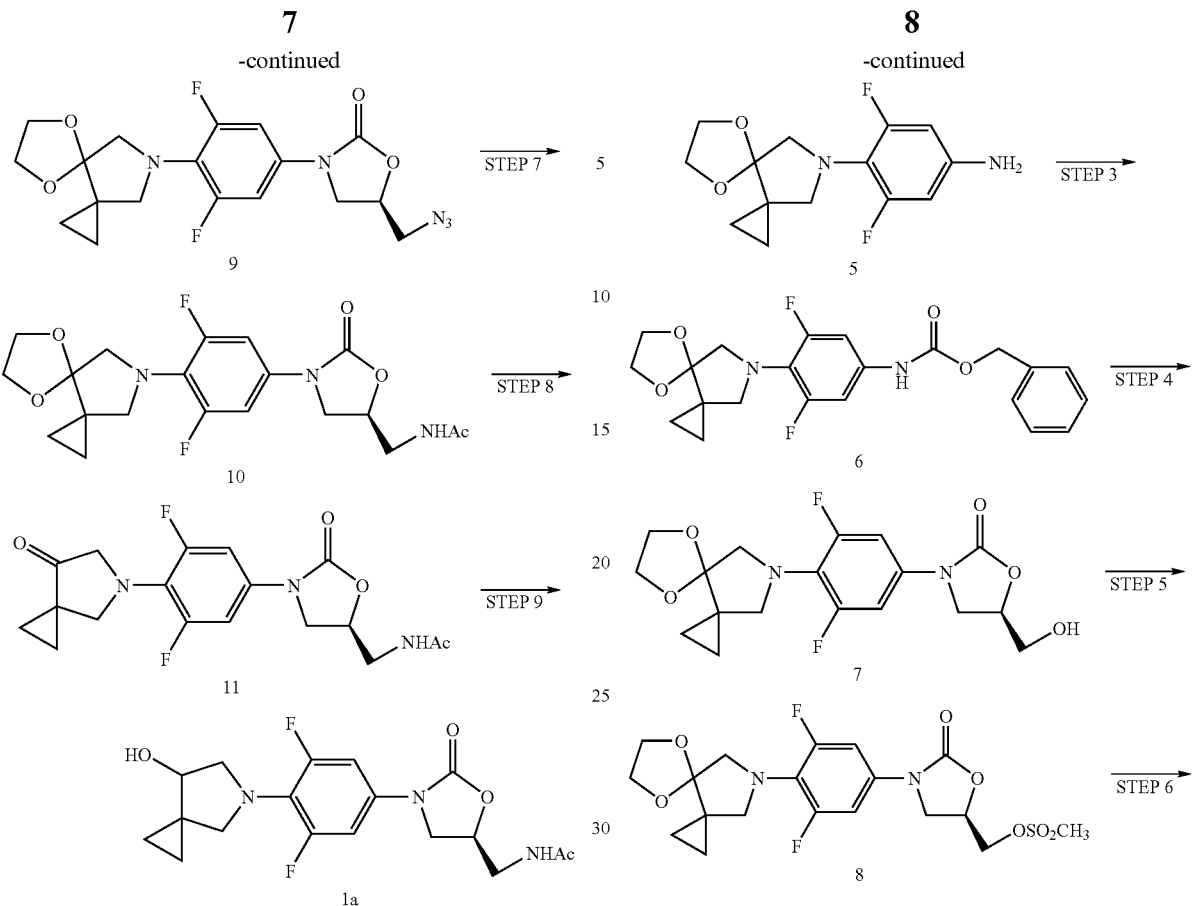
(wherein the compound of Chemical Formula 1a is included within the range of Chemical Formula 1)
The method according to the present invention, as illustrated in the following Reaction Scheme 2, may further comprise:
halogenating or aminating the compound of Chemical Formula 1a to a compound of Chemical Formula 1b (Step 10) after Step 9.
[Reaction Scheme 2]
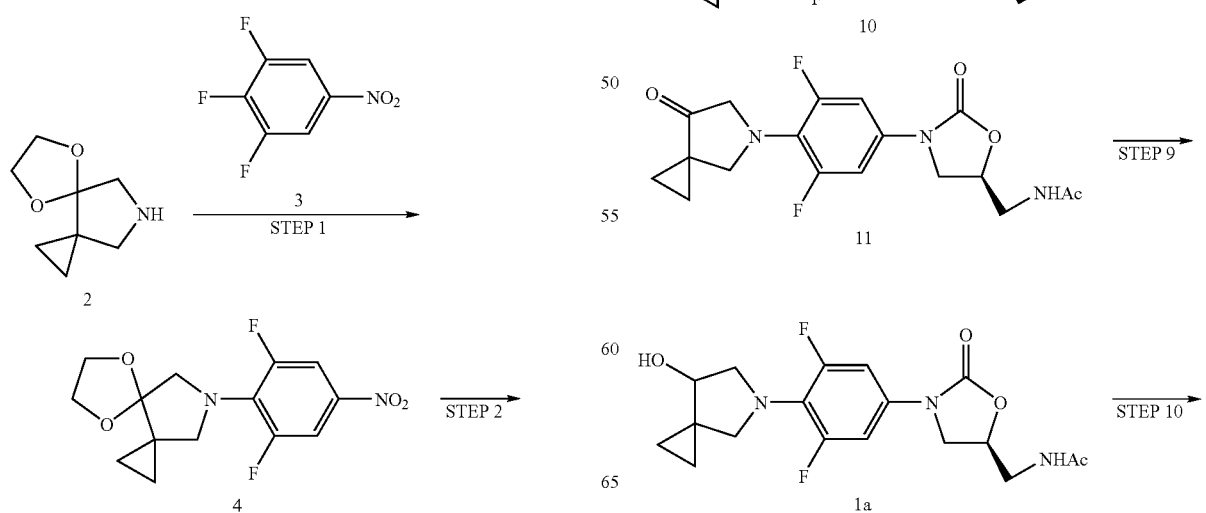

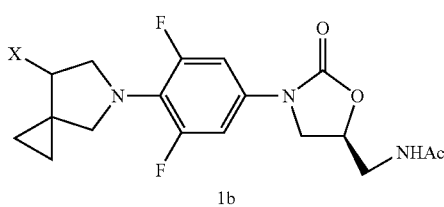
1b (wherein X is a halogen or an amine, and the compounds of Chemical Formulas 1a and 1b are included within the range of Chemical Formula 1.)

Also, the method according to the present invention, as illustrated in the following Reaction Scheme 3, may further comprise:

Reacting the compound of Chemical Formula 11 with an amine chloride salt to give a compound of Chemical Formula 1c (Step 9') after Step 8.

[Reaction Scheme 3]

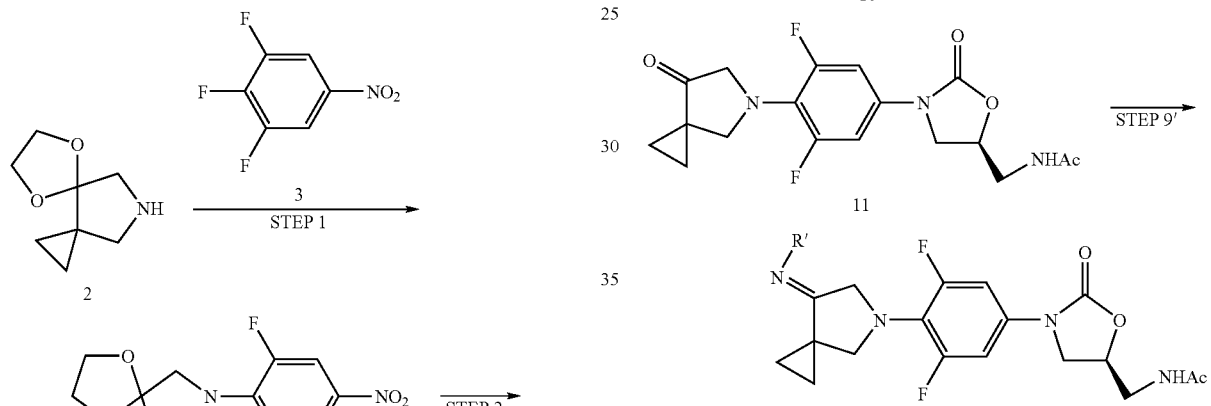

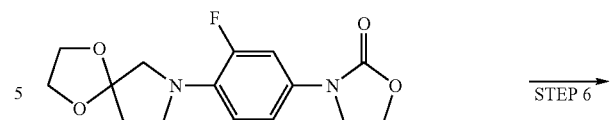
8

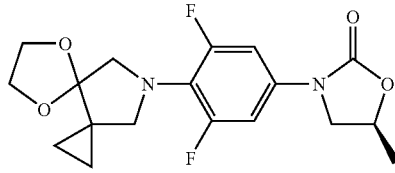
9

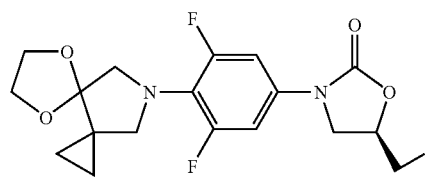
10

11

1c (wherein R' is a hydroxy, methoxy or amine group, and the compound of Chemical Formula 1c is included within the range of Chemical Formula 1.)

When R' is a hydroxy, as illustrated in the following Reaction Scheme 4, the method may further comprises:

Reacting a nucleophile with the compound of Chemical Formula 1c in the presence of a base to give a compound of Chemical Formula 1d (Step 10') after Step 9'.

[Reaction Scheme 4]

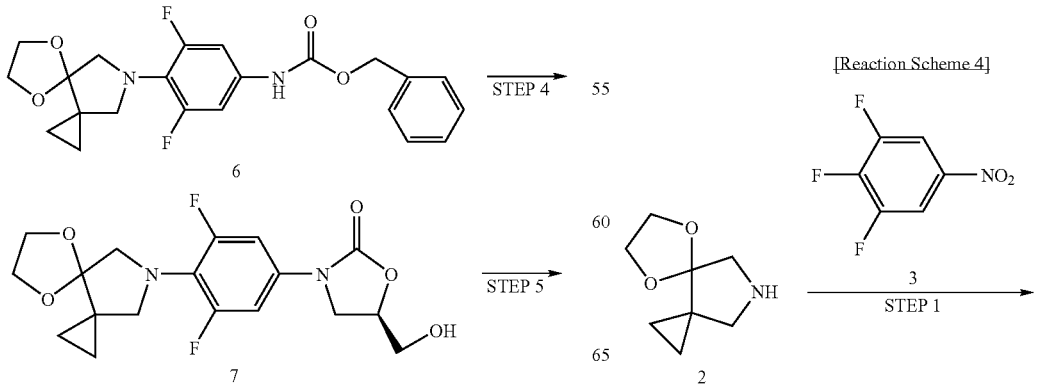

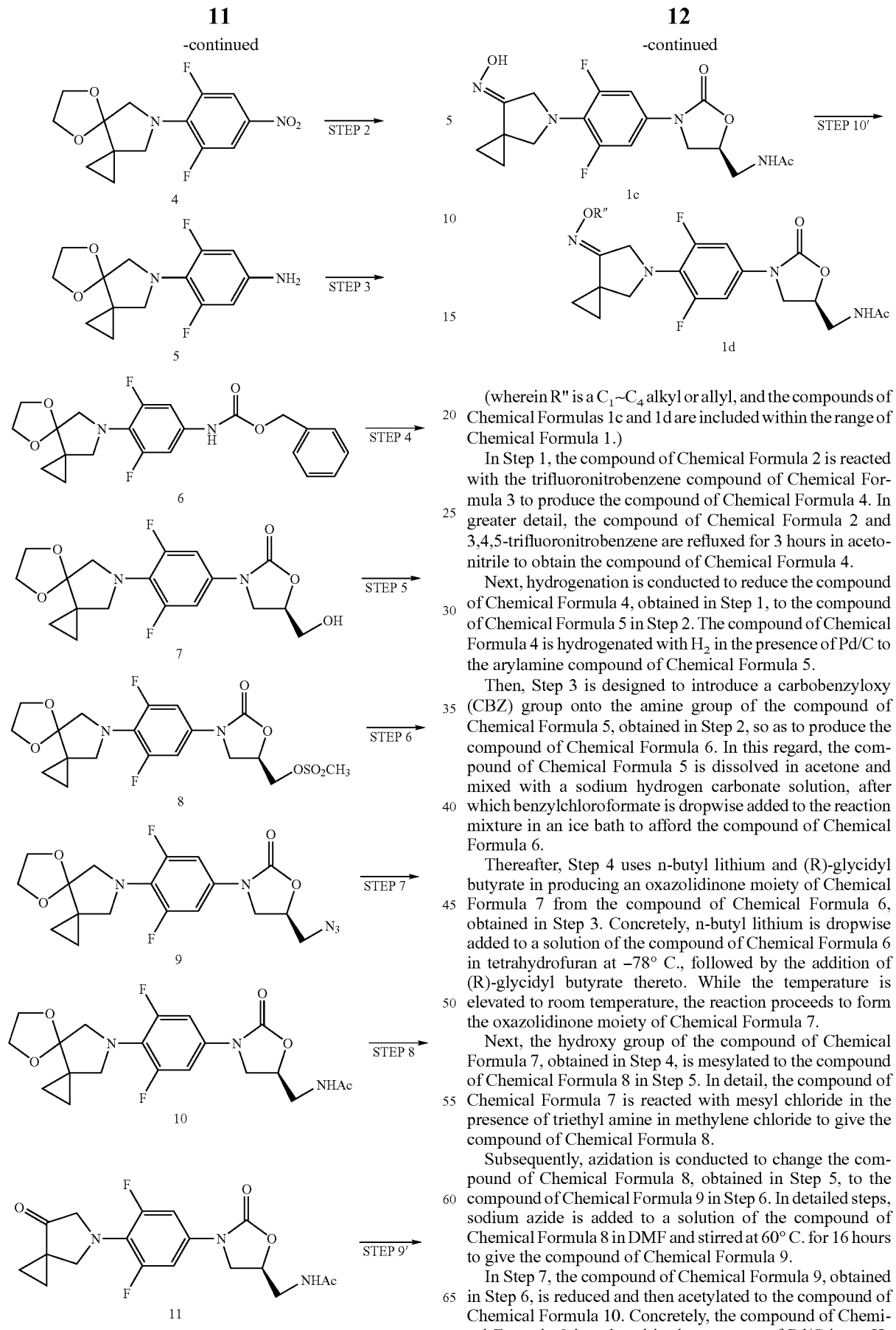

(wherein R″ is a $C_1$~$C_4$ alkyl or allyl, and the compounds of Chemical Formulas 1c and 1d are included within the range of Chemical Formula 1.)

In Step 1, the compound of Chemical Formula 2 is reacted with the trifluoronitrobenzene compound of Chemical Formula 3 to produce the compound of Chemical Formula 4. In greater detail, the compound of Chemical Formula 2 and 3,4,5-trifluoronitrobenzene are refluxed for 3 hours in acetonitrile to obtain the compound of Chemical Formula 4.

Next, hydrogenation is conducted to reduce the compound of Chemical Formula 4, obtained in Step 1, to the compound of Chemical Formula 5 in Step 2. The compound of Chemical Formula 4 is hydrogenated with $H_2$ in the presence of Pd/C to the arylamine compound of Chemical Formula 5.

Then, Step 3 is designed to introduce a carbobenzyloxy (CBZ) group onto the amine group of the compound of Chemical Formula 5, obtained in Step 2, so as to produce the compound of Chemical Formula 6. In this regard, the compound of Chemical Formula 5 is dissolved in acetone and mixed with a sodium hydrogen carbonate solution, after which benzylchloroformate is dropwise added to the reaction mixture in an ice bath to afford the compound of Chemical Formula 6.

Thereafter, Step 4 uses n-butyl lithium and (R)-glycidyl butyrate in producing an oxazolidinone moiety of Chemical Formula 7 from the compound of Chemical Formula 6, obtained in Step 3. Concretely, n-butyl lithium is dropwise added to a solution of the compound of Chemical Formula 6 in tetrahydrofuran at −78° C., followed by the addition of (R)-glycidyl butyrate thereto. While the temperature is elevated to room temperature, the reaction proceeds to form the oxazolidinone moiety of Chemical Formula 7.

Next, the hydroxy group of the compound of Chemical Formula 7, obtained in Step 4, is mesylated to the compound of Chemical Formula 8 in Step 5. In detail, the compound of Chemical Formula 7 is reacted with mesyl chloride in the presence of triethyl amine in methylene chloride to give the compound of Chemical Formula 8.

Subsequently, azidation is conducted to change the compound of Chemical Formula 8, obtained in Step 5, to the compound of Chemical Formula 9 in Step 6. In detailed steps, sodium azide is added to a solution of the compound of Chemical Formula 8 in DMF and stirred at 60° C. for 16 hours to give the compound of Chemical Formula 9.

In Step 7, the compound of Chemical Formula 9, obtained in Step 6, is reduced and then acetylated to the compound of Chemical Formula 10. Concretely, the compound of Chemical Formula 9 is reduced in the presence of Pd/C in an $H_2$ atmosphere, followed by acetylation with pyridine and anhydrous acetic acid to produce the compound of Chemical Formula 10.

Step 8 is deprotection of the compound of Chemical Formula 10, obtained in Step 7, forming the compound of Chemical Formula 11. For this, the compound of Chemical Formula 10 is dissolved in p-toluene sulfonic acid monohydrate and refluxed for 3 hours to give the compound of Chemical Formula 11.

Afterwards, reduction is performed on the compound of Chemical Formula 11 obtained in Step 8 to give the compound of Chemical Formula 1a. In more detail, with the aid of $NaBH_4$, the oxo group of the compound of Chemical Formula 11 is reduced to the hydroxy group of the compound of Chemical Formula 1a.

In Step 10, the compound of Chemical Formula 1a obtained in Step 9 is halogenated or aminated to the compound of Chemical Formula 1b. For instance, DAST may be used to substitute the hydroxy group of the compound of Chemical Formula 1a with a fluoro group. Alternatively, the hydroxy group of the compound of Chemical Formula 1a may be mesylated by reaction with amine and mesyl chloride, then azidated with sodium azide, and then reduced to an amine in the presence of palladium.

On the other hand, in Step 9', the compound of Chemical Formula 11 obtained in Step 8 is reacted with an amine chloride salt to produce the compound of Chemical Formula 1c. For instance, the compound of Chemical Formula 11 may be dissolved in ethanol, mixed with a 50% aqueous hydroxylamine solution, sodium ethoxide and water, and refluxed for 5 hours to give the hydroxyimine compound. Alternatively, the compound of Chemical Formula 11 may be dissolved in methanol and reacted with a 30~35% methoxylamine chloride salt and triethyl amine at room temperature for 10 hours with stirring to give a methoxyimine compound. In an additional alternative, the compound of Chemical Formula 11 is reacted with hydrazine chloride in the presence of triethyl amine in ethanol to afford a hydrazine compound.

In Step 10', the compound of Chemical Formula 1c obtained in Step 9' is used as a nucleophile to conduct a nucleophilic substitution in the presence of a base, leading to the compound of Chemical Formula 1d. In greater detail, when the compound of Chemical Formula 1c is a hydroxyimine compound, it is reacted with ethyl bromide or allyl bromide in the presence of potassium hydroxide to give an ethoxyimine compound or allyloxyimine compound.

For the identification of the oxazolidinone derivatives or intermediates therefor prepared as explained above in accordance with the present invention, various analytical technologies including IR spectrometry, NMR spectrometry, mass spectrometry, liquid chromatography, X-ray crystallography, optical rotation, and comparison between calculated and measured values from elemental analysis of typical compounds may be performed.

In accordance with a further aspect thereof, the present invention provides an antibiotic composition containing the oxazolidinone derivative or a pharmaceutically acceptable salt thereof as an active ingredient.

In accordance with still a further aspect thereof, the present invention provides a method for the treatment of bacterial diseases by administering an oxazolidinone derivative represented by Chemical Formula 1 or a pharmaceutically acceptable salt thereof at a therapeutically effective dose to a subject in need thereof.

In accordance with a further aspect thereof, the present invention provides a method for killing a bacterial strain infecting a subject, comprising administering the oxazolidinone derivative represented by Chemical Formula 1 or a pharmaceutically acceptable salt thereof at a therapeutically effective dose to a subject in need thereof.

The oxazolidinone derivatives or pharmaceutically acceptable salts thereof, useful as active ingredients in the antibiotic composition according to the present invention, were found to have anti-bacterial activity as potent as or more potent than that of the commercially available antibiotic Linezolid as they were measured to range in MIC from 0.781 to 3.125 mg/ml in an in vitro assay. Particularly, they showed an MIC of 0.781 mg/ml against Gram-positive bacteria including *Haemophilus influenza* and non-pathogenic Coagulase negative staphylococci as well as resistant bacteria including vancomycin resistant enterococci (VRE), which has a higher inhibitory activity to Linezolid (MIC: 1.563~3.125 mg/ml) (see Table 2). Accordingly, the oxazolidinone derivatives according to the present invention are useful as novel antibiotics.

For clinical practice, the pharmaceutical composition containing the oxazolidinone derivative or a pharmaceutically acceptable salt thereof in accordance with the present invention may be formulated into the following oral or non-oral dosage forms, but are not limited thereto.

Oral dosage preparations of the compounds of the present invention may take the form of tablets, pills, hard/soft capsules, solutions, suspensions, emulsions, syrups, granules, elixirs and the like. These dosage forms may comprise diluents (e.g., lactose, dextrose, sucrose, manitol, sorbitol, cellulose and/or glycine), lubricants (e.g., silica, talc, stearic acid and magnesium or calcium salts thereof, and/or polyethylene glycol) in addition to the active ingredient. For example, tablets may further comprise a binder, such as magnesium aluminum silicate, starch paste, gelatin, methyl cellulose, sodium carboxyethyl cellulose, and/or polyvinylpyrrolidone, and optionally a disintegrant such as starch, agar, alginic acid or sodium salts thereof or an effervescent mixture and/or an adsorbent, a colorant, a flavor, and a sweetener.

The pharmaceutical composition containing the derivative of Chemical Formula 1 as an active ingredient may be administered in a non-oral manner. Non-oral dosage forms may be injections via subcutaneous, intravenous, intramuscular, or intrathoracic routes.

As for non-oral dosage forms, they may be prepared by mixing the oxazolidinone derivative of Chemical Formula 1 or pharmaceutically acceptable salt thereof with a stabilizer or buffer in water and loading the solution or suspension onto ampule or vial unit forms. The composition intended for oral or non-oral administration is sterilized or sterile and may comprise auxiliary agents such as preservatives, stabilizers, wetable powders or emulsifying agents, osmosis-adjusting salts, and/or buffers, and other therapeutically useful agents. It may be formulated using admixture, granulation or coating methods.

The effective dosage of the active ingredient in accordance with the present invention depends on various factors, including the patient's age, weight, gender, route of administration, state of health, severity of diseases, etc. Typically, the compound according to the present invention may be administered at a daily dose ranging from 0.01 to 1,000 mg and preferably from 1 to 500 mg for 70 kg adult patients. The compound may be administered in a single dose or may be divided into multiple doses per day according to the instructions of a physician or pharmacist.

EXAMPLE 1

Preparation of (S)—N-{{3-[3,5-Difluoro-4-(7-hydroxy-5-azaspiro[2,4]heptan-5-yl)phenyl]-2-oxo-5-oxazolidinyl}methyl}acetamide

Step 1: Preparation of 3,5-difluoro-4(7,7-ethylenedioxy-5-azaspiro[2,4]heptan-5-yl)nitrobenzen To a solution of 7,7-ethylenedioxy-5-azaspiro[2,4]heptane in acetonitrile (50 mL) was dropwise added 3,4,5-trifluoronitrobenzene (5.3 g, 31.6 mmol) and the reaction mixture was refluxed for 3 hours. After the reaction was terminated, the reaction mixture was cooled to room temperature and the solvent was removed therefrom by vacuum distillation. It was diluted with ethyl acetate and water, and the organic phase thus formed was dried over magnesium sulfate. The residue was filtered, concentrated in a vacuum, and purified through column chromatography (n-hexane/ethyl acetate=4:1) to afford the target compound (3.5 g, yield 66%).

$^1$H-NMR (300 MHz, CDCl$_3$) δ 0.66 (t, 2H, J=5.3 Hz), 0.95 (t, 2H, J=5.3 Hz), 3.67 (d, 2H, J=2.3 Hz), 3.75 (d, 2H, J=3.5 Hz), 3.97 (s, 4H), 7.49 (s, 1H), 7.90 (s, 1H); $^{13}$C-NMR (300 MHz, CDCl$_3$) δ 8.1, 25.3, 56.4, 58.3, 65.4, 112.1, 112.5, 112.9, 121.8, 141.9, 147.5, 150.7.

Steps 2~3: Preparation of N-carbobenzyloxy-[3,5-difluoro-4-(7,7-ethylenedioxy-5-azaspiro[2,4]heptan-5-yl)phenyl]aniline (S)—N-{{3-[3,5-difluoro-4-(7-hydroxy-5-azaspiro[2,4]heptan-5-yl)phenyl]-2-oxo-5-oxazolidinyl}methyl}acetamide (2.5 g, 8.5 mmol), obtained in Step 1, was placed together with 10% Pd/C (1.3 g, 50%) in a Paar shaker flask and dissolved in THF (60 mL), followed by shaking for 2 hours at H$_2$ 40 psi. After the reaction terminated, the reaction mixture was filtered through cellite and the filtrate was distilled in a vacuum to remove the solvent therefrom before performing the following sequential processes. To a solution of the product in acetone (40 mL) was added a 10% NaHCO$_3$ solution (2 mL), and then droplets of benzylchloroformate (1.6 mL, 11.4 mmol) in an ice bath. When the reaction terminated after stirring at room temperature for 3 hours, the solvent was removed by vacuum distillation. The residue was dissolved in ethyl acetate and mixed with water and the organic phase thus obtained was dried over anhydrous magnesium sulfate. After filtration, the filtrate was distilled in a vacuum to remove the solvent, followed by purification through column chromatography (n-hexane/ethyl acetate=5:1) to afford the target compound (1.9 g, yield 55%).

$^1$H-NMR (300 MHz, CDCl$_3$) δ 0.64 (t, 2H, J=5.3 Hz), 0.93 (t, 2H, J=5.3 Hz), 3.45 (s, 2H), 3.56 (d, 2H, J=1.7 Hz), 3.93 (s, 4H), 5.18 (s, 2H), 7.49 (s, 1H), 7.90 (s, 1H); $^{13}$C-NMR (300 MHz, CDCl$_3$) δ 8.6, 25.7, 57.0, 59.3, 65.0, 66.9, 108.6, 112.8, 112.9, 115.1, 115.2, 128.3, 128.5, 128.9, 133.6, 136.2, 150.5, 153.7.

Step 4: Preparation of (R)—{N-3-[3,5-difluoro-4-(7,7-ethylenedioxy-5-azaspiro[2,4]heptan-5-yl)phenyl]-2-oxo-5-oxazolidinyl}

To a solution of N-carbobenzyloxy-[3,5-difluoro-4-(7,7-ethylenedioxy-5-azaspiro[2,4]heptan-5-yl)phenyl]aniline (2.1 g, 5.1 mmol), obtained in Step 3, in purified tetrahydrofuran (50 mL) was dropwise added 1.6 M n-butyl lithium-hexane solution (3.5 mL, 5.6 mmol) at −78° C. 10 min later, droplets of (R)-glycidyl butyrate (0.8 mL, 4.7 mmol) were slowly added. The temperature was elevated to room temperature with stirring for 16 hours. After the reaction terminated, the reaction mixture was mixed with a saturated aqueous ammonium chloride solution (10 mL) and then extracted with ethyl acetate and water. The organic phase thus formed was dried over anhydrous magnesium sulfate and filtered. After the removal of the solvent through vacuum distillation, the filtrate was purified using column chromatography (n-hexane/ethyl acetate=1:1) to afford the target compound (1.3 g, yield 66%).

$^1$H-NMR (300 MHz, CDCl$_3$) δ 0.64 (t, 2H, J=5.4 Hz), 0.94 (t, 2H, J=5.4 Hz), 3.47 (d, 2H, J=1.5 Hz), 3.57 (d, 2H, J=2.4 Hz), 3.88 (d, 2H, J=8.5 Hz), 3.94 (s, 4H), 3.97 (d, 2H, J=8.5 Hz), 4.71 (m, 1H), 7.15 (s, 1H), 7.30 (s, 1H); $^{13}$C-NMR (300 MHz, CDCl$_3$) δ 8.6, 25.6, 46.6, 59.1, 62.7, 65.1, 72.9, 107.7, 108.1, 112.8, 114.5, 114.6, 129.0, 133.8, 150.2, 154.9.

Step 5: Preparation of (R)—{N-3-[3,5-difluoro-4-(7,7-ethylenedioxy-5-azaspiro[2,4]heptan-5-yl)phenyl]-2-oxo-5-oxazolidinyl}methyl methanesulfonate To a methylenechloride solution (50 mL) of (R)—{N-3-[3,5-difluoro-4-(7,7-ethylenedioxy-5-azaspiro[2,4]heptan-5-yl)phenyl]-2-oxo-5-oxazolidinyl}methanol (1.3 g, 3.4 mmol), obtained in Step 4, was added triethylamine (1.1 mL, 7.8 mmol) and then droplets of mesylchloride (0.4 mL, 4.4 mmol) in an ice bath, followed by stirring at room temperature for 3 hours. After the reaction terminated, the reaction mixture was extracted with methylene chloride and water and the organic phase thus formed was dried over anhydrous magnesium sulfate and filtered. The filtrate was concentrated in a vacuum to remove the solvent therefrom and purified through column chromatography (n-hexane/ethyl acetate=1:1) to afford the target compound (0.9 g, yield 62%).

$^1$H-NMR (300 MHz, CDCl$_3$) δ 0.62 (t, 2H, J=5.4 Hz), 0.91 (t, 2H, J=5.4 Hz), 3.08 (s, 3H), 3.46 (d, 2H, J=1.6 Hz), 3.55 (d, 2H, J=2.1 Hz), 3.85 (t, 2H, J=4.6 Hz), 3.92 (s, 4H), 4.07 (t, 2H, J=8.9 Hz), 4.87 (m, 1H), 7.15 (s, 1H), 7.30 (s, 1H); $^{13}$C-NMR (300 MHz, CdCl$_3$) δ 8.6, 25.6, 37.7, 46.8, 56.8, 59.0, 65.1, 68.4, 69.5, 108.3, 112.7, 114.8, 128.3, 128.4, 134.2, 150.1, 153.8.

Step 6: Preparation of (R)—{N-3-[3,5-difluoro-4-(7,7-ethylenedioxy-5-azaspiro[2,4]heptan-5-yl)phenyl]-2-oxo-5-oxazolidinyl}methyl azide To a solution of (R)—{N-3-[3,5-difluoro-4-(7,7-ethylenedioxy-5-azaspiro[2,4]heptan-5-yl)phenyl]-2-oxo-5-oxazolidinyl}methyl methanesulfate (0.9 g, 2.1 mmol), obtained in Step 5, in DMF (20 mL) was added sodium azide (0.5 g, 8.0 mmol), followed by heating at 60° C. for 16 hours. After the reaction terminated, the reaction mix was cooled to room temperature and let to stand for 30 min and extracted with ethyl acetate and water. The organic phase thus formed was dried over anhydrous magnesium sulfate and filtered. The filtrate was distilled in a vacuum to remove the solvent therefrom and purified through column chromatography (n-hexane/ethyl acetate=1:1) to afford the target compound (0.6 g, yield 65%).

$^1$H-NMR (300 MHz, CDCl$_3$) δ 0.63 (t, 2H, J=5.3 Hz), 0.92 (t, 2H, J=5.3 Hz), 3.48 (s, 2H), 3.56 (d, 2H, J=6.3 Hz), 3.78 (t, 2H, J=7.5 Hz), 3.93 (s, 4H), 4.02 (t, 2H, J=8.9 Hz), 4.75 (m, 1H), 7.15 (s, 1H), 7.30 (s, 1H); $^{13}$C-NMR (300 MHz, CDCl$_3$) δ 8.6, 25.6, 47.8, 53.1, 56.9, 65.1, 70.5, 108.2, 112.7, 114.8, 114.9, 128.7, 134.1, 150.2, 154.0.

Step 7: Preparation of (S)—N-{{3-[3,5-difluoro-4-(7,7-ethylenedioxy-5-azaspiro[2,4]heptan-5-yl)phenyl]-2-oxo-5-oxazolidinyl}methyl}acetamide To a solution of (R)—{N-3-[3,5-difluoro-4-(7,7-ethylenedioxy-5-azaspiro[2,4]heptan-5-yl)phenyl]-2-oxo-5-oxazolidinyl}methylazide (0.6 g, 1.6 mmol), obtained in Step 6, in ethyl acetate (15 mL) was added 10% palladium-charcoal (30 mg) and the reaction mixture was stirred at room temperature under 1 atm of $H_2$, for 14 hours. When the reaction terminated, the solvent was removed by vacuum distillation. After the reducing atmosphere was changed to a nitrogen atmosphere, the reaction mixture was added with pyridine (0.2 mL, 1.9 mmol) and anhydrous acetic acid (0.5 mL, 5.3 mmol) and stirred at 0° C. for 30 min and then at room temperature for 2 hours. When the reaction terminated, the reaction mixture was filtered through cellite, and the filtrate was distilled in a vacuum to remove the solvent therefrom, followed by purification through column chromatography (n-hexane/ethyl acetate=1:2) to afford the target compound (0.5 g, yield 84%).
$^1$H-NMR (300 MHz, $CDCl_3$) δ 0.64 (t, 2H, J=5.3 Hz), 0.92 (t, 2H, J=5.3 Hz), 2.03 (s, 3H), 3.46 (s, 2H), 3.56 (d, 2H, J=2.4 Hz), 3.71 (t, 2H, J=7.3 Hz), 3.94 (s, 4H), 4.00 (t, 2H, J=9.0 Hz), 4.75 (m, 1H), 7.15 (s, 1H), 7.30 (s, 1H); $^{13}$C-NMR (300 MHz, $CDCl_3$) δ 8.6, 22.9, 25.6, 41.9, 47.8, 56.8, 59.0, 65.1, 71.9, 108.1, 112.7, 114.8, 114.9, 128.8, 134.0, 150.1, 154.7, 171.4.

Step 8: Preparation of (S)—N-{{3-[3,5-difluoro-4-(7-oxo-5-azaspiro[2,4]heptan-5-yl)phenyl]-2-oxo-5-oxazolidinyl}methyl}acetamide To a solution of (S)—N-{{3-[3,5-difluoro-4-(7,7-ethylenedioxy-5-azaspiro[2,4]heptan-5-yl)phenyl]-2-oxo-5-oxazolidinyl}methyl}acetamide (0.5 g, 1.4 mmol), obtained in Step 7, in a mixture of acetone (40 mL) and water (10 mL) was added p-toluenesulfonic acid monohydrate (0.5 g, 2.7 mmol), followed by refluxing for 3 hours. When the reaction terminated, the reaction mixture was distilled in a vacuum to remove the solvent therefrom. After the addition of triethyl amine (1 mL), extraction was conducted with methylene chloride. The organic phase was dried over anhydrous magnesium sulfate and filtered The filtrate was concentrated in a vacuum and purified through column chromatography (n-hexane/ethyl acetate=1:2) to afford the target compound (0.3 g, yield 45%).
$^1$H-NMR (300 MHz, $CDCl_3$) δ 1.17 (q, 2H, J=3.6 Hz), 1.44 (q, 2H, J=3.5 Hz), 2.02 (s, 3H), 3.67 (t, 2H, J=3.0 Hz), 3.75 (t, 2H, J=7.8 Hz), 3.96 (d, 2H, J=1.6 Hz), 4.02 (t, 2H, J=8.9 Hz), 4.77 (m, 1H), 7.19 (s, 1H), 7.35 (s, 1H); $^{13}$C-NMR (300 MHz, $CDCl_3$) δ 18.1, 23.2, 41.9, 47.7, 55.3, 58.3, 71.8, 108.1, 114.4, 115.9, 130.5, 133.1, 151.0, 154.4, 171.2, 212.3.

Step 9: Preparation of (S)—N-{{3-[3,5-difluoro-4-(7-hydroxy-5-azaspiro[2,4]heptan-5-yl)phenyl]-2-oxo-5-oxazolidinyl}methyl}acetamide To a solution of (S)—N-{{3-[3,5-difluoro-4-(7-oxo-5-azaspiro[2,4]heptan-5-yl)phenyl]-2-oxo-5-oxazolidinyl}methyl}acetamide (120 mg, 3.3 mol), obtained in Step 8, in tetrahydrofuran (15 mL) was slowly added sodium borohydride (12.6 mg, 3.3 mol) in an ice bath, followed by stirring for 2 hours. When the reaction terminated, the reaction mixture was neutralized with acetic acid and extracted with ethyl acetate and water. The organic phase thus formed was dried over anhydrous magnesium sulfate and filtered. After the removal of the solvent by vacuum distillation, the filtrate was purified through flat-TLC (n-hexane/ethyl acetate=1:1) to afford the target compound (94 mg, yield 77%).
$^1$H-NMR (300 MHz, $CDCl_3$) δ 1.17 (q, 2H, J=3.6 Hz), 1.44 (q, 2H, J=3.5 Hz), 2.02 (s, 3H), 3.5 (s, 1H), 3.67 (t, 2H, J=3.0 Hz), 3.75 (t, 2H, J=7.8 Hz), 3.96 (d, 2H, J=1.6 Hz), 4.02 (t, 2H, J=8.9 Hz), 4.77 (m, 1H), 7.19 (s, 1H), 7.35 (s, 1H); $^{13}$C-NMR (300 MHz, $CDCl_3$) δ 18.1, 23.2, 41.9, 47.7, 55.3, 58.3, 71.8, 108.1, 114.4, 115.9, 130.5, 133.1, 151.0, 154.4, 171.2.

EXAMPLE 2

Preparation of (S)—N-{{3-[3,5-Difluoro-4-(7-fluoro-5-azaspiro[2,4]heptan-5-yl)phenyl]-2-oxo-5-oxazolidinyl}methyl}acetamide To a solution of (S)—N-{{3-[3,5-difluoro-4-(7-hydroxy-5-azaspiro[2,4]heptan-5-yl)phenyl]-2-oxo-5-oxazolidinyl}methyl}acetamide (94.0 mg, 2.6 mol), obtained in Example 1, in methylene chloride (10 mL) was dropwise added DAST (0.2 mL, 3.0 mol) in an ice bath, followed by stirring at room temperature for 3 hours. When the reaction terminated, the reaction mixture was extracted with water. The organic phase thus formed was distilled in a vacuum to remove the solvent therefrom and purified through flat-TLC (n-hexane/ethyl acetate=1:1) to afford the target compound (47 mg, yield 11%).
$^1$H-NMR (300 MHz, $CDCl_3$) δ 1.17 (q, 2H, J=3.6 Hz), 1.44 (q, 2H, J=3.5 Hz), 2.02 (s, 3H), 3.4 (s, 1H), 3.67 (t, 2H, J=3.0 Hz), 3.75 (t, 2H, J=7.8 Hz), 3.96 (d, 2H, J=1.6 Hz), 4.02 (t, 2H, J=8.9 Hz), 4.77 (m, 1H), 7.19 (s, 1H), 7.35 (s, 1H); $^{13}$C-NMR (300 MHz, $CDCl_3$) δ 18.1, 23.2, 41.9, 47.7, 55.3, 58.3, 71.8, 108.1, 114.4, 115.9, 130.5, 133.1, 151.0, 154.4, 171.2.

EXAMPLE 3

Preparation of (S)—N-{{3-[3,5-Difluoro-4-(7-hydroxyimino-5-azaspiro[2,4]heptan-5-yl)phenyl]-2-oxo-5-oxazolidinyl}methyl}acetamide To a solution of (S)—N-{{3-[3,5-difluoro-4-(7-oxo-5-azaspiro[2,4]heptan-5-yl)phenyl]-2-oxo-5-oxazolidinyl}methyl}acetamide (60.0 mg, 0.2 mmol), obtained in Step 8 of Example 1, in ethanol were added $NH_2OH$ HCl (37.0 mg, 5.1 mmol), $CH_3CO_2Na$ (40.0 mg, 5.1 mmol) and water, followed by refluxing for 5 hours. When the reaction terminated, the reaction mixture was cooled to room temperature and extracted with ethyl acetate and water. The organic phase thus formed was dried over anhydrous magnesium sulfate. After the removal of the solvent by vacuum distillation, the residue was purified through flat-TLC (n-hexane/ethyl acetate=1:1) to afford the target compound (27 mg, yield 41%).
$^1$H-NMR (300 MHz, $CDCl_3$) δ 1.17 (q, 2H, J=3.6 Hz), 1.44 (q, 2H, J=3.5 Hz), 2.02 (s, 3H), 3.67 (t, 2H, J=3.0 Hz), 3.75 (t, 2H, J=7.8 Hz), 3.96 (d, 2H, J=1.6 Hz), 4.02 (t, 2H, J=8.9 Hz), 4.77 (m, 1H), 7.19 (s, 1H), 7.35 (s, 1H); $^{13}$C-NMR (300 MHz, $CDCl_3$) δ 18.1, 23.2, 41.9, 47.7, 55.3, 58.3, 71.8, 108.1, 114.4, 115.9, 130.5, 133.1, 151.0, 154.4, 171.2.

EXAMPLE 4

Preparation of (S)—N-{{3-[3,5-Difluoro-4-(7-methoxyimino-5-azaspiro[2,4]heptan-5-yl)phenyl]-2-oxo-5-oxazolidinyl}methyl}acetamide To a solution of (S)—N-{{3-[3,5-difluoro-4-(7-oxo-5-azaspiro[2,4]heptan-5-yl)phenyl]-2-oxo-5-oxazolidinyl}methyl}acetamide (60.0 mg, 0.2 mmol), obtained in Step 8 of Example 1, in methanol was added triethylamine (0.1 mL, 0.6 mmol), followed by stirring for 10 min. Then, the mixture was slowly added with droplets of methoxylamine chloride (0.04 mL, 0.5 mmol) in an ice bath and then stirred at room temperature for 12 hours. After the reaction terminated, the solvent was removed by vacuum distillation and the reaction mix was extracted with methylene chloride and water. The organic phase thus formed was dried over anhydrous magnesium sulfate and filtered. After concentration by vacuum distillation, the filtrate was purified through flat-TLC (n-hexane/ethyl acetate=1:1) to afford the target compound (30 mg, yield 47%).

$^1$H-NMR (300 MHz, CDCl$_3$) δ 1.17 (q, 2H, J=3.6 Hz), 1.44 (q, 2H, J=3.5 Hz), 2.02 (s, 3H), 3.67 (t, 2H, J=3.0 Hz), 3.75 (t, 2H, J=7.8 Hz), 3.96 (d, 2H, J=1.6 Hz), 4.02 (t, 2H, J=8.9 Hz), 4.77 (m, 1H), 7.19 (s, 1H), 7.35 (s, 1H); $^{13}$C-NMR (300 MHz, CDCl$_3$) δ 18.1, 23.2, 41.9, 47.7, 55.3, 58.3, 71.8, 108.1, 114.4, 115.9, 130.5, 133.1, 151.0, 154.4, 171.2, 212.3.

EXAMPLE 5

Preparation of (S)—N-{{3-[3,5-Difluoro-4-(7-hydrazino-5-azaspiro[2,4]heptan-5-yl)phenyl]-2-oxo-5-oxazolidinyl}methyl}acetamide A solution of (S)—N-{{3-[3,5-difluoro-4-(7-oxo-5-azaspiro[2,4]heptan-5-yl)phenyl]-2-oxo-5-oxazolidinyl}methyl}acetamide (60.0 mg, 0.2 mmol), obtained in Step 8 of Example 1, in ethanol was added with triethyl amine (0.1 mL, 0.7 mmol) and stirred for 10 min, and then slowly added with droplets of hydrazine acid chloride (45.0 mg, 0.5 mmol) in an ice bath and stirred for 3 hours. After the reaction terminated, the reaction mixture was distilled in a vacuum to remove the solvent therefrom and extracted with ethyl acetate and water. The organic phase thus obtained was dried over anhydrous magnesium sulfate, filtered and concentrated in a vacuum. Purification of the concentrate through flat-TLC (n-hexane/ethylacetate=1:1) afforded the target compound (22 mg, yield 35%).

$^1$H-NMR (300 MHz, CDCl$_3$) δ 1.17 (q, 2H, J=3.6 Hz), 1.44 (q, 2H, J=3.5 Hz), 2.02 (s, 3H), 3.67 (t, 2H, J=3.0 Hz), 3.75 (t, 2H, J=7.8 Hz), 3.96 (d, 2H, J=1.6 Hz), 4.02 (t, 2H, J=8.9 Hz), 4.77 (m, 1H), 7.19 (s, 1H), 7.35 (s, 1H); $^{13}$C-NMR (300 MHz, CDCl$_3$) δ 18.1, 23.2, 41.9, 47.7, 55.3, 58.3, 71.8, 108.1, 114.4, 115.9, 130.5, 133.1, 151.0, 154.4, 171.2, 212.3.

EXAMPLE 6

Preparation of (S)—N-{{3-[3,5-Difluoro-4-(7-ethoxyimino-5-azaspiro[2,4]heptan-5-yl)phenyl]-2-oxo-5-oxazolidinyl}methyl}acetamide While being maintained at 0° C., KOH (0.13 g, 2.4 mmol) was added to a solution of the (S)—N-{{3-[3,5-difluoro-4-(7-hydroxydimono?-5-azaspiro[2,4]heptan-5-yl)phenyl]-2-oxo-5-oxazolidinyl}methyl}acetamide (0.8 g, 1.4 mmol) obtained in Example 3 in 10 mL of DMF, and then slowly droplets of ethyl bromide (0.4 mL, 5.6 mmol) were added with stirring for 3 hours. After the reaction terminated, the reaction mixture was poured into cold water and extracted with ethyl acetate. The organic phase was washed with water and brine and dehydrated over anhydrous magnesium sulfate. Purification through flash column chromatography (n-hexane/ethyl acetate=1:4) afforded the target compound in a white pure form (0.52 g).

$^1$H-NMR (300 MHz, CDCl$_3$) δ 1.06-1.25 (m, 5H), 1.44 (q, 2H, J=3.5 Hz), 2.02 (s, 3H), 3.67 (t, 2H, J=3.0 Hz), 3.75 (t, 2H, J=7.8 Hz), 4.02-4.07 (m, 4H), 4.77 (m, 1H), 7.19 (s, 1H), 7.35 (s, 1H).

EXAMPLE 7

Preparation of (S)—N-{{3-[3,5-Difluoro-4-(7-allyloxyimino-5-azaspiro[2,4]heptan-5-yl)phenyl]-2-oxo-5-oxazolidinyl}methyl}acetamide The same procedure as Example 6, with the exception that allyl bromide was used instead of ethyl bromide, to afford the target compound (yield 67%).

$^1$H-NMR (300 MHz, CDCl$_3$) δ 1.14 (q, 2H, J=3.8 Hz), 1.45 (q, 2H, J=3.3 Hz), 2.05 (s, 3H), 3.67 (t, 2H, J=3.0 Hz), 3.75 (t, 2H, J=7.8 Hz), 4.38-4.45 (m, 5H), 5.11-5.19 (m, 4H), 5.78-5.84 (m, 2), 4.77 (m, 1H), 7.19 (s, 1H), 7.35 (s, 1H).

EXAMPLE 8

Preparation of (S)—N-{{3-[3,5-difluoro-4-(7-amino-5-azaspiro[2,4]heptan-5-yl)phenyl]-2-oxo-5-oxazolidinyl}methyl}acetamide A solution of (S)—N-{{3-[3,5-difluoro-4-(7-hydroxy-5-azaspiro[2,4]heptan-5-yl)phenyl]-2-oxo-5-oxazolidinyl}methyl}acetamide (1.3 g, 3.4 mmol), obtained in Example 1, in methylene chloride (50 mL) was admixed with triethyl amine (1.1 mL, 7.8 mmol) and then droplets of mesyl chloride (0.4 mL, 4.4 mmol) were added thereto in an ice bath with stirring at room temperature for 3 hours. After the reaction terminated, the reaction mixture was extracted with methylene chloride and water, ant the organic phase thus formed was dried over anhydrous magnesium sulfate and filtered. After the removal of the solvent therefrom through vacuum distillation, the filtrate was purified through column chromatography (n-hexane/ethyl acetate=1:1).

This purified compound (0.9 g, 2.1 mmol) was dissolved in DMF (20 mL) and reacted with sodium azide (0.5 g, 8.0 mmol) with heating at 60° C. for 16 hours. After the reaction terminated, the reaction mixture was cooled at room temperature for 30 min and extracted with ethyl acetate and water. The organic phase thus formed was dried over anhydrous magnesium sulfate and filtered. After the removal of the solvent by vacuum distillation, the filtrate was purified through column chromatography (n-hexane/ethyl acetate=1:1).

In turn, this purified compound (0.6 g, 1.6 mmol) was dissolved in ethyl acetate (15 mL) and mixed with 10% palladium-charcoal (30 mg) before stirring at room temperature for 14 hours under 1 atm of H$_2$. After the reaction terminated, the solvent was removed by vacuum distillation. The reducing atmosphere was changed to a nitrogen atmosphere, after which to the reaction mixture were added pyridine (0.2 mL, 1.9 mmol) and anhydrous acetic acid (0.5 mL, 5.3 mmol) with stirring at 0° C. for 30 min and then stirring at room temperature for 2 hours. After the reaction terminated, the reaction mixture was filtered through cellite. After the removal of the solvent by vacuum distillation, the filtrate was purified through column chromatography (n-hexane/ethyl acetate=1:2) to afford the target compound (yield 34%).

$^1$H-NMR (300 MHz, CDCl$_3$) δ 1.19 (q, 2H, J=3.4 Hz), 1.46 (q, 2H, J=3.5 Hz), 2.02 (s, 3H), 3.67 (t, 2H, J=3.0 Hz), 3.70 (t, 2H, J=7.8 Hz), 3.96 (d, 2H, J=1.5 Hz), 4.02 (t, 2H, J=8.6 Hz), 4.74 (m, 1H), 7.19 (s, 1H), 7.35 (s, 1H); $^{13}$C-NMR (300 Mz,

CDCl$_3$) δ 18.1, 23.2, 41.6, 47.5, 55.3, 58.0, 71.8, 108.1, 114.0, 115.2, 130.5, 133.1, 151.0, 154.4, 171.2, 212.3.

EXPERIMENTAL EXAMPLE

Assay for Anti-Bacterial Activity

The oxazolidinone derivatives according to the present invention were assayed for inhibitory activity against various bacteria as described in the following.

To this end, the compound of Example 2 and the currently used oxazolidinone class Linezolid were examined for minimal inhibitory concentration (hereinafter, referred to as "MIC") against Gram-positive strains and resistant bacteria including methicillin-resistant *Staphylococcus aureus* (MRSA) and vancomycin resistant enterococci by an agar dilution method using Muller-Hinton agar.

As used herein, the term MIC is intended to refer to the lowest concentration of an antibiotic that will inhibit the growth of a microorganism. MIC values are expressed as μg/ml. Bacterial strains used for this assay included *Haemophilus influenza*, Coagulase negative staphylococi, *Staphylcoccus aureus* (MRSA), *Enterococcus faecalis* (VER), *Enterococcus faecium* (VR 1, VR 2), and Vancomycin resistant enterococci 1~6.

After being incubated for 18 hours in a Muller-Hinton broth, the strains were transferred to fresh broth at a concentration of approximately 10$^7$ CFU/ml. Isolates were distributed with a multipoint inoculator (MIC-2000 Dynatech) at 10$^4$ CFU per spot onto agar plates containing the compound of the Examples or Comparative Examples. MICs were determined, and the results are summarized in Table 2, below.

TABLE 2

| Strains | Inhibitory Activity (MIC, mg/ml) | |
| --- | --- | --- |
| | C. Example (Linezolid) | Example 2 |
| a | 3.125 | 0.781 |
| b | 3.125 | 0.781 |
| c | 1.563 | 1.563 |
| d | 1.563 | 1.563 |
| e | 1.563 | 1.563 |
| f | 1.563 | 1.563 |
| g | 1.563 | 3.125 |
| h | 1.563 | 1.563 |
| i | 1.563 | 3.125 |
| j | 1.563 | 0.781 |
| k | 1.563 | 0.781 |
| l | 1.563 | 0.781 | a: *Haemophilus infuenz*)
b: Coagulase negative*staphylococi*)
c: *Staphylcoccus aureus* (MRSA))
d: *Enterococcus faecalis* (VRE)
e: *Enterococcus faecium* (VR 1)
f: *Enterococcus faecium* (VR 2)
g: Vancomycin resistant *enterococci* 1
h: Vancomycin resistant *enterococci* 2
i: Vancomycin resistant *enterococci* 3
j: Vancomycin resistant *enterococci* 4
k: Vancomycin resistant *enterococci* 5
l: Vancomycin resistant *enterococci* 6

As shown in Table 2, the oxazolidinone derivative according to the present invention was found to have have antibacterial activity as potent as or more potent than that of the commercially available antibiotic Linezolid because its MIC was within the range of 0.781~3.125 mg/ml. Particularly, the oxazolidinone derivative according to the invention showed an MIC of 0.781 mg/ml against Gram-positive bacteria including *Haemophilus influenza* and non-pathogenic Coagulase negative staphylococci as well as resistant bacteria including vancomycin resistant enterococci (VRE), which is superior in inhibitory activity to Linezolid (SC: 1.563~3.125 mg/ml). Accordingly, the oxazolidinone derivatives according to the present invention are useful as novel antibiotics.

Depending on the purposes for which they are used, dosages of the oxazolidinone derivatives of Chemical Formula 1 according to the present invention may be formulated in various forms. Formulation examples are given to illustrate dosage preparations containing the compounds of Chemical Formula 1 as active ingredients and not to limit the scope of the present invention.

Formulation Example 1

Tablet (Direct Compression)

After being sieved, 5.0 mg of the active ingredient was mixed with 14.1 mg of lactose, 0.8 mg of crospovidone, 0.8 mg of USNF and 0.1 mg of magnesium stearate, and directly compressed into tablets.

Formulation Example 2

Tablet (Wet Granulation)

5.0 mg of the active ingredient was sieved and mixed with 16.0 mg of lactose and 4.0 mg of starch. To this mixture was added a suitable amount of a solution of 0.3 mg of polysorbate 80 in pure water, followed by micro granulation. The micro granules thus obtained were dried, sieved, and mixed with 2.7 mg of colloidal silicon dioxide and 2.0 mg of magnesium stearate. The mixture was compressed into tablets.

Formulation Example 3

Powder and Capsule

After being sieved, 5 mg of the active ingredient was admixed with 14.8 mg of lactose, 10.0 mg of polyvinyl pyrrolidone and 0.2 mg of magnesium stearate. The admixture was loaded into hard No. 5 gelatin capsules using a suitable device.

Formulation Example 4

Injection

An injection comprising 180 mg of mannitol, 26 mg of Na$_2$HPO$_4$. 12H$_2$O and 2974 mg of distilled water in addition to 100 mg of the active ingredient was prepared.

Exhibiting potent inhibitory activity against Gram positive bacteria including *Haemophilus influenza* and non-pathogenic Coagulase negative staphylococci, as well as resistant bacteria including VRE, as described above, the oxazolidinone derivatives or pharmaceutically acceptable salts thereof in accordance with the present invention are usable as an active ingredient for antibiotics.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An oxazolidinone compound, represented by Chemical Formula 1 below, or a pharmaceutically acceptable salt thereof:

[Chemical Formula 1]

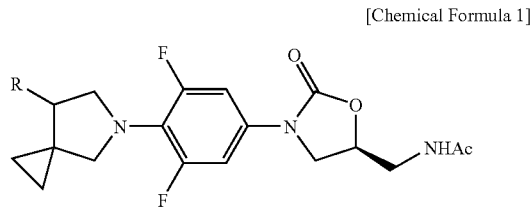

wherein R is a hydroxy, an amino, a halogen, hydrazine, a hydroxyimine, an alkyloxyimine of C1-C4 or an allyloxyimine.

2. The oxazolidinone compound or the pharmaceutically acceptable salt thereof according to claim 1, wherein R is fluoro.

3. The oxazolidinone compound or the pharmaceutically acceptable salt thereof according to claim 1, wherein the oxazolidinone compound is (S)—N-{{3-[3,5-fluoro-4-(7-fluoro-5-azaspiro[2,4]heptan-5-yl)phenyl]-2-oxo-5-oxazolidinyl}methyl}acetamide.

4. The oxazolidinone compound or the pharmaceutically acceptable salt thereof according to claim 1, wherein R is methoxyimine, ethoxyimine, propoxyimine, isopropoxyimine, butoxyimine, isobutoxyimine or allyloxyimine.

5. The oxazolidinone compound or the pharmaceutically acceptable salt thereof according to claim 1, wherein the oxazolidinone compound is (S)—N-{{3-[3,5-difluoro-4-(7-hydroxy-5-azaspiro[2,4]heptan-5-yl)phenyl]-2-oxo-5-oxazolidinyl}methyl}acetamide.

6. The oxazolidinone compound or the pharmaceutically acceptable salt thereof according to claim 1, wherein the oxazolidinone compound is (S)—N-{{3-[3,5-difluoro-4-(7-hydroxyimino-5-azaspiro[2,4]heptan-5-yl)phenyl]-2-oxo-5-oxazolidinyl}methyl}acetamide.

7. The oxazolidinone compound or the pharmaceutically acceptable salt thereof according to claim 1, wherein the oxazolidinone compound is (S)—N-{{3-[3,5-difluoro-4-(7-methoxyimino-5-azaspiro[2,4]heptan-5-yl)phenyl]-2-oxo-5-oxazolidinyl}methyl}acetamide.

8. The oxazolidinone compound or the pharmaceutically acceptable salt thereof according to claim 1, wherein the oxazolidinone compound is (S)—N-{{3-[3,5-difluoro-4-(7-hydrazino-5-azaspiro[2,4]heptan-5-yl)phenyl]-2-oxo-5-oxazolidinyl}methyl}acetamide.

9. The oxazolidinone compound or the pharmaceutically acceptable salt thereof according to claim 1, wherein the oxazolidinone compound is (S)—N-{{3-[3,5-difluoro-4-(7-ethoxyimino-5-azaspiro[2,4]heptan-5-yl)phenyl]-2-oxo-5-oxazolidinyl}methyl}acetamide.

10. The oxazolidinone compound or the pharmaceutically acceptable salt thereof according to claim 1, wherein the oxazolidinone compound is (S)—N-{{3-[3,5-difluoro-4-(7-allyloxyimino-5-azaspiro[2,4]heptan-5-yl)phenyl]-2-oxo-5-oxazolidinyl}methyl}acetamide.

11. The oxazolidinone compound or the pharmaceutically acceptable salt thereof according to claim 1, wherein the oxazolidinone compound is (S)—N-{{3-[3,5-difluoro-4-(7-amino-5-azaspiro[2,4]heptan-5-yl)phenyl]-2-oxo-5-oxazolidinyl}methyl}acetamide.

12. The oxazolidinone compound or the pharmaceutically acceptable salt thereof according to claim 1, further comprising a diluent selected from the group consisting of lactose, dextrose, sucrose, manitol, sorbitol, cellulose and glycine.

13. The oxazolidinone compound or the pharmaceutically acceptable salt thereof according to claim 1, further comprising a lubricant selected from the group consisting of silica, talc, stearic acid, a magnesium salt, a calcium salt, and polyethylene glycol.

14. The oxazolidinone compound or the pharmaceutically acceptable salt thereof according to claim 1, further comprising a binder selected from the group consisting of magnesium aluminum silicate, starch paste, gelatin, methyl cellulose, sodium carboxymethyl cellulose, and polyvinylprrolidone.

15. The oxazolidinone compound or the pharmaceutically acceptable salt thereof according to claim 1, further comprising a disintegrant selected from the group consisting of starch, agar, alginic acid, and a sodium salt.

16. The oxazolidinone compound or the pharmaceutically acceptable salt thereof according to claim 1, further comprising an adsorbent.

17. The oxazolidinone compound or the pharmaceutically acceptable salt thereof according to claim 1, further comprising a colorant.

18. The oxazolidinone compound or the pharmaceutically acceptable salt thereof according to claim 1, further comprising a flavor and a sweetener.

19. The oxazolidinone compound or the pharmaceutically acceptable salt thereof according to claim 1, further comprising an auxiliary agent selected from the group consisting of a preservative, a stabilizer, a wetable powder, an emulsifying agent, an osmosis-adjusting salt, and a buffer.

20. The oxazolidinone compound or the pharmaceutically acceptable salt thereof according to claim 1, wherein the oxazolidinone compound or the pharmaceutically acceptable salt is in a form of a tablet, a pill, a hard/soft capsule, a solution, a suspension, an emulsion, a syrup, a granule, and an elixir.

* * * * *